US008043356B2

(12) United States Patent  
Kölbel et al.

(10) Patent No.: US 8,043,356 B2  
(45) Date of Patent: Oct. 25, 2011

(54) STENT-GRAFT AND APPARATUS AND FITTING METHOD

(75) Inventors: Tilo Kölbel, Malmo (SE); Martin Malina, Malmo (SE); Kim Moegelvang Jensen, Koebenhavn (DK); Bent Øhlenschlaeger, Li. Skensved (DK); Erik E. Rasmussen, Slagelse (DK)

(73) Assignee: Cook Medical Technologies LLC, Bloomington, IN (US)

( * ) Notice: Subject to any disclaimer, the term of this patent is extended or adjusted under 35 U.S.C. 154(b) by 98 days.

(21) Appl. No.: 12/384,362

(22) Filed: Apr. 3, 2009

(65) Prior Publication Data

US 2009/0259291 A1  Oct. 15, 2009

Related U.S. Application Data

(60) Provisional application No. 61/123,531, filed on Apr. 9, 2008.

(51) Int. Cl.  
*A61F 2/82* (2006.01)

(52) U.S. Cl. ....................................... 623/1.13

(58) Field of Classification Search .................. 623/1.13; A61F 2/06  
See application file for complete search history.

(56) References Cited

U.S. PATENT DOCUMENTS

| 6,974,471 | B2 | 12/2005 | Van Schie et al. | |
|---|---|---|---|---|
| 2003/0088305 | A1* | 5/2003 | Van Schie et al. | 623/1.12 |
| 2007/0043425 | A1* | 2/2007 | Hartley et al. | 623/1.12 |

FOREIGN PATENT DOCUMENTS

| EP | 0897699 | 2/1999 |
|---|---|---|
| WO | WO 03/034948 | 5/2003 |

OTHER PUBLICATIONS

Int'l Search Report PCT/US2009/002098, Oct. 20, 2009, EPO.  
Written Opinion PCT/US2009/002098, Oct. 20, 2009, EPO.

* cited by examiner

*Primary Examiner* — Thomas J Sweet  
*Assistant Examiner* — Jason-Dennis Stewart  
(74) *Attorney, Agent, or Firm* — Brinks Hofer Gilson & Lione

(57) ABSTRACT

A stent-graft (100) is provided with a tightenable loop element (104) having a first end terminated in a slip knot or self-tightening knot (112) and a second end which is received in and can slide in the knot (112). The knot (112) is tied by a suture to the stent-graft (100) so as to be fixed thereto. The loop (104) is fitted to the stent-graft (100) in a manner as to pass between the inside to the outside of the graft material and in such a manner that controlled curvature of the stent-graft (100) is possible, in particular control of the overlapping of adjacent stents held within the zone of the loop (104). An introducer assembly is also disclosed which includes a control cannula (120) able to the fixed to the stent-graft (100) during the deployment procedure, as well as a mechanism of suture loops (150, 152) at the proximal end of the stent-graft (100) for retaining this in a constricted form during the process of curving the latter during the deployment process.

24 Claims, 9 Drawing Sheets

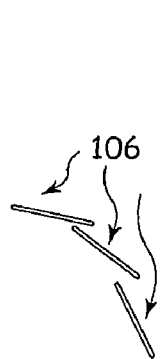
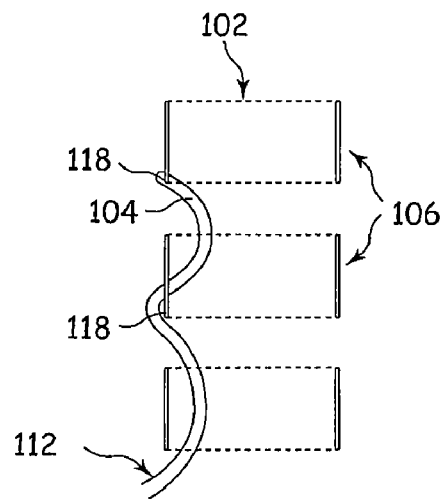
Fig. 7B
Fig. 7A
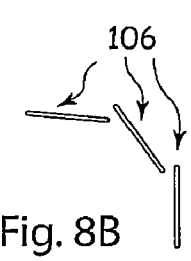
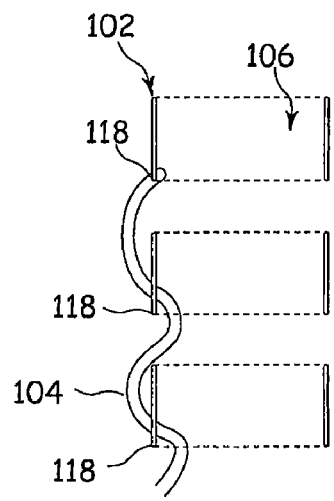
Fig. 8B
Fig. 8A
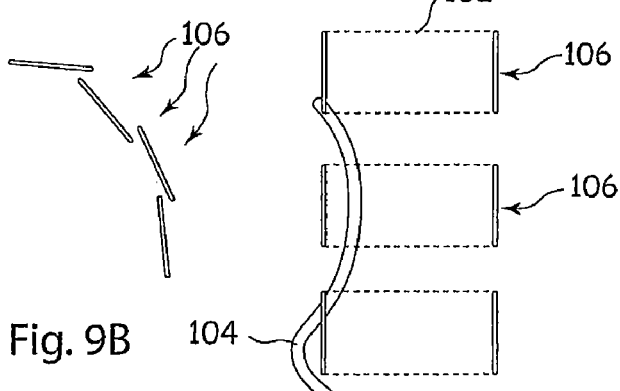
Fig. 9B
Fig. 9A
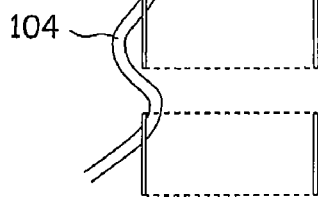
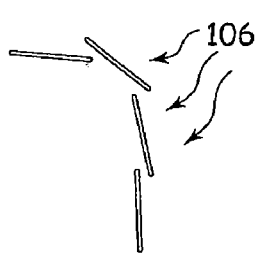
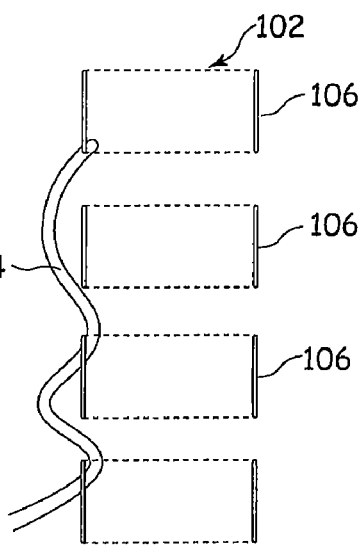
Fig. 10B
Fig. 10A

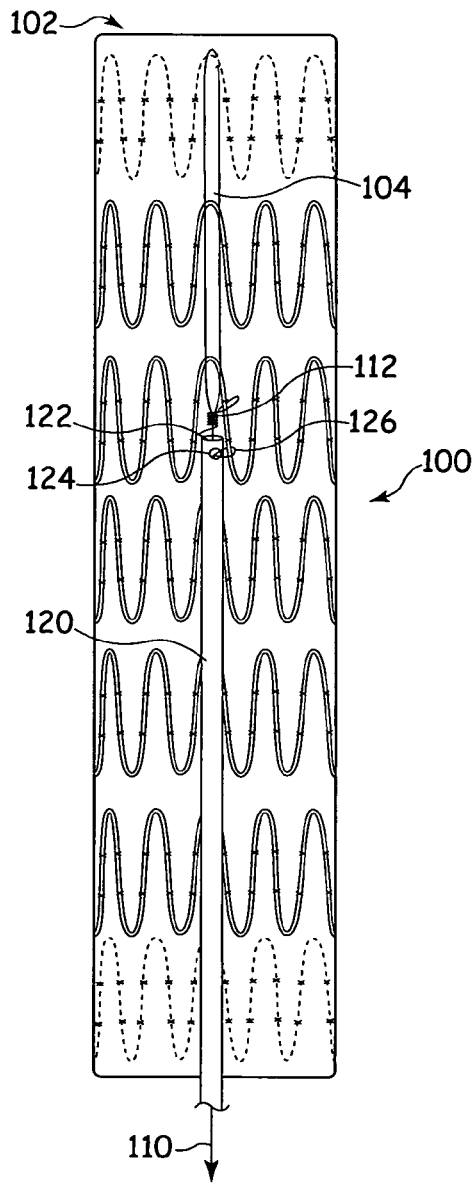
Figure 11
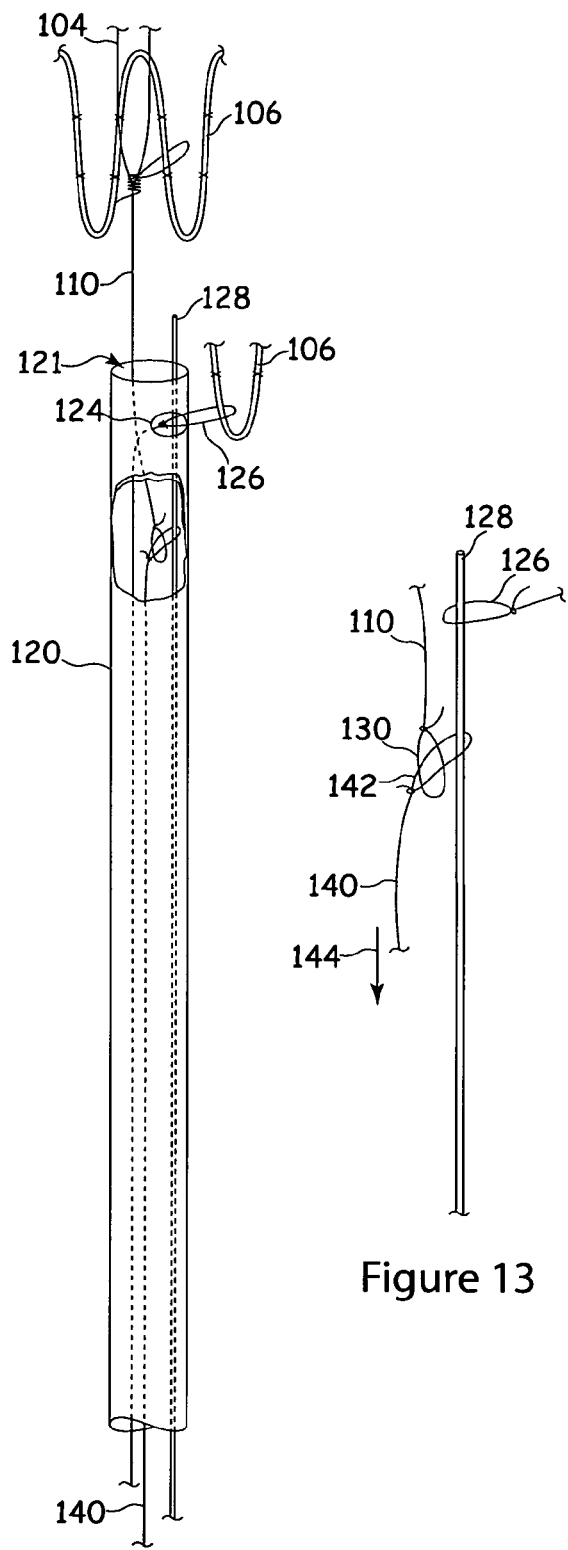
Figure 12
Figure 13

US 8,043,356 B2

STENT-GRAFT AND APPARATUS AND FITTING METHOD

CROSS-REFERENCE TO RELATED APPLICATIONS

This application claims priority of provisional application Ser. No. 61/123,531, filed Apr. 9, 2008.

TECHNICAL FIELD

The present invention relates to an implantable medical device such as a stent-graft, stent or similar device as well as to apparatus for and a method of fitting such a device into a lumen of a patient, particularly into a highly curved lumen such as the aortic arch and into locations which provide little room for error in the placement of the device, such as lumens having short necks of healthy vascular wall.

BACKGROUND OF THE INVENTION

Prostheses for the repair of vascular defects, including for example vascular aneurysms, are well known in the art. A common prosthesis for treatment of such a medical condition is a stent-graft.

Prostheses of this type are typically deployed endoluminally through a vein or artery adjacent a surface of a patient, aortic prostheses, for example, being commonly fed through the femoral artery. A generally accepted method of deployment involves the location of a guide wire along the path to be followed by the introducer assembly, up to the site in the vasculature to be treated. Once the guide wire is in place, a series of catheters is advanced along the guide wire, finally with the introduction of a catheter assembly which carries the stent or stent-graft to be fitted. The catheters have sufficient trackability to follow the guide wire along the curves and turns of the patient's vasculature and some can also curve sufficiently so as to be able to fit a stent-graft, for example, into a highly curved vessel such as the aortic arch.

Even though such a procedure is possible into the aortic arch, it is mired in difficulties as a result of the tight curvature of the aorta in this location. One such difficulty arises in connection with the proximal end of the stent-graft, which is liable to be incorrectly fitted such that it incompletely seals around the inner wall of the aorta as a result of the curvature imparted to the stent-graft. This can lead to leakage of blood around the outside of the stent-graft and thus a less than effective treatment. Furthermore, as a result of the non-optimal placement of the stent-graft using known procedures, there is a limit to the length of neck of healthy vascular wall which is needed to provide a seal around the proximal end of the stent-graft. This limits the application of such stent-grafts, in particular for the treatment of aneurysms close to a branch vessel. In addition, in some instances at least, a part of the proximal end of the stent-graft can remain loosely located in the vessel, leading to premature fatigue failure and thrombus effects.

Attempts have been made to resolve these difficulties. For instance, in the applicant's U.S. Pat. No. 6,974,471, mechanisms are described for imparting a curvature to the stent-graft at the moment of its deployment.

The deployment of stent-grafts and other devices, particularly in the aortic arch, in lumens having short necks of healthy vascular wall and other difficult pathologies also requires very precise placement of the device to ensure a good coupling to healthy tissue and in particular a coupling which has longevity and which provides a fluid tight seal with the vessel wall. Prior art systems do allow for a certain amount of coarse re-positioning of the device. However, if the device is not fitted precisely in position, the procedure may need to be repeated, for example by withdrawing the device back into its delivery introducer (where this is possible) and starting the deployment operation afresh. Repeating the procedure increases operating time, trauma to the patient and still does not guarantee a successful outcome. In some instances, it is necessary to abort the procedure.

SUMMARY OF THE INVENTION

The present invention seeks to provide and improved implantable medical device and an improved system for and method of fitting a stent-graft or other device to a patient.

According to an aspect of the present invention, there is provided an implantable medical device including a compressible and curvable structure; a loop of suture material, the loop including a first end closed in a knot and a second end passing through the knot and able to slide therein at least in a loop tightening direction, the loop being fitted to the device such that tightening of the loop causes the device to be curved; and including a tie element which ties the knot to a part of the medical device.

The loop enables the medical device to be compressed on one side so as to cause it to curve. In the case of a stent-graft, the device can be made to curve so as to fit the curvature of the aortic arch, for instance. The provision of a tie element to tie the knot of the loop ensures that the loop can be tightened without the need for any other knot holding device.

Preferably, the knot is one of a slip knot and a self-tightening knot. A slip knot removes the loop biasing force from the device after deployment and allows this to bend together with the lumen in which the device is fitted. A self-tightening knot ensures that the medical device retains a minimum curvature even after deployment. Both alternatives have advantages in particular medical applications.

Preferably, the device is provided with a plurality of stents coupled to one another by resilient means, the loop being fitted so as to be held to a surface of the device at a plurality of positions adjacent portions said stents so as to pull said stents together such that at least some of said stents overlap one another in a predetermined manner when the loop is tightened so as to cause folding of the resilient means between adjacent stents.

In the preferred embodiment, the device is a stent-graft, the resilient means being graft fabric between adjacent stents.

Advantageously, the loop is fitted to the device so as to cause overlap of adjacent stents held in the loop.

In one embodiment, the loop is fitted so as to cause trailing ends of stents to slide over leading edges of their adjacent stents in a direction from a proximal end to a distal end of the device.

In another embodiment, the loop is fitted so as to cause trailing ends of stents to slide under leading edges of their adjacent stents in a direction from a proximal end to a distal end of the device.

The loop may be fitted so as to cause at least one of the stents to be pulled between stents located either side thereof.

Preferably, said at least one stent is pulled to a position underlying the stents adjacent thereto so as to lie on an outside of the device. In another embodiment, said at least one stent is pulled to a position overlying the stents adjacent thereto so as to lie on an inside of the device.

In one embodiment, the loop is fitted to the medical device so as to pass a plurality of times between an internal space of the device to outside thereof, thereby to cause the device to compress or fold in locations between transitions points of the loop from the inside to the outside of the device.

Arranging the loop in this manner provides for much better control of the curvature of the medical device compared to known arrangements in which the loop is located either substantially wholly on the outside of the device or on the inside. By having the loop feed a plurality of times between the inside to the outside of the device, more controlled compression of the device at the side of the loop is possible.

There is preferably also provided a constriction device for constricting a proximal end of the device during curvature thereof.

Such a constricting device is particularly useful for devices which have barbs or other anchoring devices at their proximal end, in which case the constricting device can prevent these from engaging the vessel wall until after deployment and curvature of the device.

The constricting device may include at least one thread wrapped around the proximal end of the device, said at least one thread being releasable from a constricting arrangement to allow full deployment of the device.

According to another aspect of the present invention, there is provided an introducer assembly suitable for deploying in a lumen of a patient an implantable medical device as specified herein, including a cannula provided at a distal end thereof with an opening, a tie loop able to be held by the cannula through the opening and being tied to a part of the implantable medical device, and a release element operable to release the tie loop on deployment of the medical device.

Preferably, the release element includes a control element around which the tie loop is held to hold the tie loop to the cannula, the control element being retractable to release the tie loop from the cannula.

The control element may be a control rod or wire.

In the case of a medical device as specified herein, the cannula preferably provides a lumen for receiving the second end of the tightenable loop of the medical device.

Advantageously, the release element includes a pull cord or wire attachable to the second end of the tightenable loop.

Preferably, the release element is operable to release the second end of the tightenable loop from the pull cord.

In an embodiment, the pull cord is provided with a looped end engageable with a looped end on the second end of the tightenable loop, the looped end of the pull cord being able to be carried by the release element and releasable by withdrawal of the release element so as to detach the tightenable loop from the introducer.

The assembly may include means for releasing the or a constricting device provided to keep a proximal end of the medical device in a constricted configuration during deployment.

These means for release of the constriction device may be the control element.

According to another aspect of the present invention, there is provided an implantable medical device including a compressible and curvable structure, a loop of suture material, the loop including a first end closed in a knot and a second end passing through the knot and able to slide therein at least in a loop tightening direction, the loop being fitted to the device such that tightening of the loop causes the device to be curved, wherein the device is provided with a plurality of stents coupled to one another by resilient means, the loop being fitted so as to be held to a surface of the device at a plurality of positions adjacent portions said stents so as to pull said stents together such that at least some of said stents overlap one another in a predetermined manner when the loop is tightened so as to cause folding of the resilient means between adjacent stents.

According to another aspect of the present invention, there is provided an implantable medical device including a compressible and curvable structure, a loop of suture material, the loop including a first end closed in a knot and a second end passing through the knot and able to slide therein at least in a loop tightening direction, the loop being fitted to the device such that tightening of the loop causes the device to be curved, wherein the loop is fitted to the medical device so as to pass a plurality of times between an internal space of the device to outside thereof, thereby to cause the device to compress or fold in locations between transitions points of the loop from the inside to the outside of the device.

According to another aspect of the present invention, there is provided an implantable medical device including a compressible and curvable structure, at least one loop of suture material provided around a proximal end of the medical device, the loop having an operable length less than the diameter of the proximal end of the medical device so as in use to constrict radially the proximal end of the medical device during deployment.

Advantageously, the loop of suture material is able to be held in a constricting configuration during curvature of the medical device.

BRIEF DESCRIPTION OF THE DRAWINGS

Embodiments of the present invention are described below, by way of example only, with reference to the accompanying drawings, in which:

FIGS. 7A to 10C show various different embodiments of suture loop configurations for controlling the curvature of the proximal end of a stent-graft;

FIG. 11 is a front elevational view of an embodiment of deployment element for use in imparting curvature to a stent-graft;

FIG. 12 is an enlarged view of the deployment element of FIG. 12;

FIG. 13 is a schematic diagram of a tying rod of the deployment device of FIGS. 11 and 12.

DESCRIPTION OF THE PREFERRED EMBODIMENTS

For the purposes of this disclosure, when used in connection with description of a stent-graft or other implantable medical device, the term "proximal" refers to a part or position closest to the heart, that is upstream in the direction of blood flow, while the term "distal" refers to a part or position furthest from the heart. On the other hand, when used in connection with an introducer assembly the term "proximal" refers to a position or part closest to the surgeon and typically kept outside the patient, while the term "distal" refers to a position or part furthest from the surgeon and in practice furthest into a patient during a deployment procedure.

Figure 1:
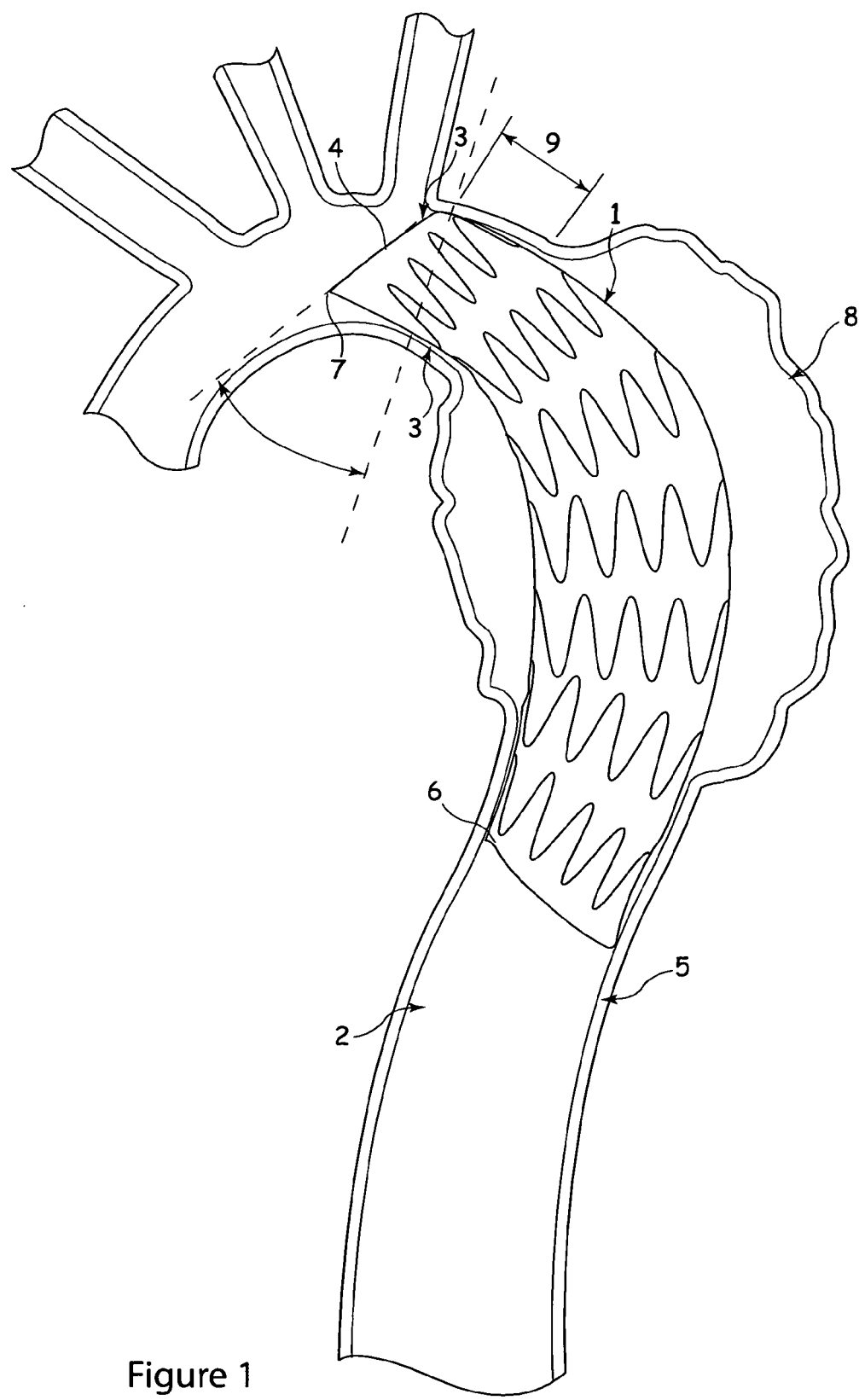
FIG. 1 shows an example of stent-graft deployed in the aortic arch by a conventional introducer system.

Referring to FIG. 1, there is shown an example of deployment of a stent-graft 1 within the aorta 2 of a patient for the treatment of, for example, an aneurysm 8. In this particular example, the stent-graft extends part-way into the aortic arch 3 at its proximal end 4, down to the thoracic aorta 5 at its distal end 6. The curvature of the aortic arch 3, coupled with use of a conventional introducer system which follows the arch 3 by being bent thereby, can cause the proximal end 4 of the stent-graft 1 to be located incorrectly, that is not to have its opening perpendicular with the vessel at that position. As a result, the inner side 7 of the stent-graft 1 stands proud of the vessel wall, being spaced therefrom. The angle A at which the proximal end 4 lies deviates from the perpendicular line B. The resultant gap between the inner side 7 and the aortic wall provides a path for leakage of blood, which can lead to failure of the stent-graft in achieving its intended function. In practice, such imprecise deployment results in it being necessary to have a relatively long neck 9 to achieve a reliable seal between the stent-graft 1 and the vessel wall. Thus, medical conditions which do not have a sufficient length of neck 9, that is of healthy vessel wall, cannot at present be treated.

In addition to these problems, the end 7 of the stent-graft tends to flap in the force of blood flow, leading to fatigue wear and to thrombus formation.

Figure 2:
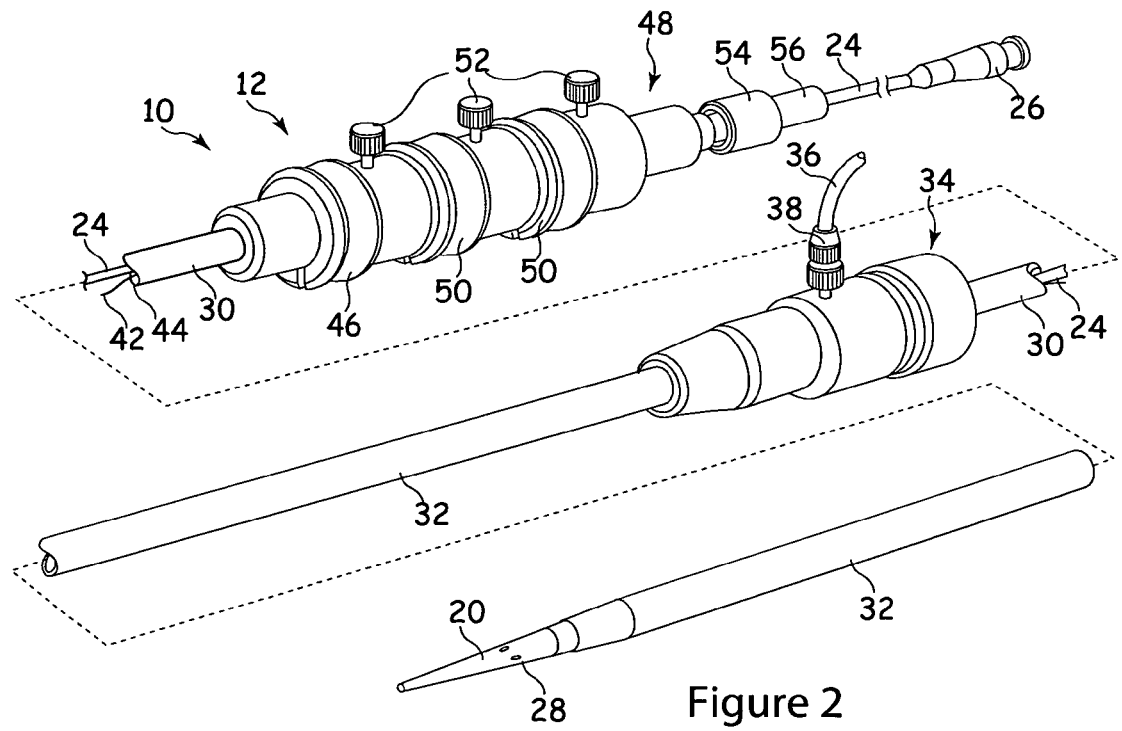
FIGS. 2 and 3 are perspective views of an example of introducer system which can be used with the present invention.
Figure 3:
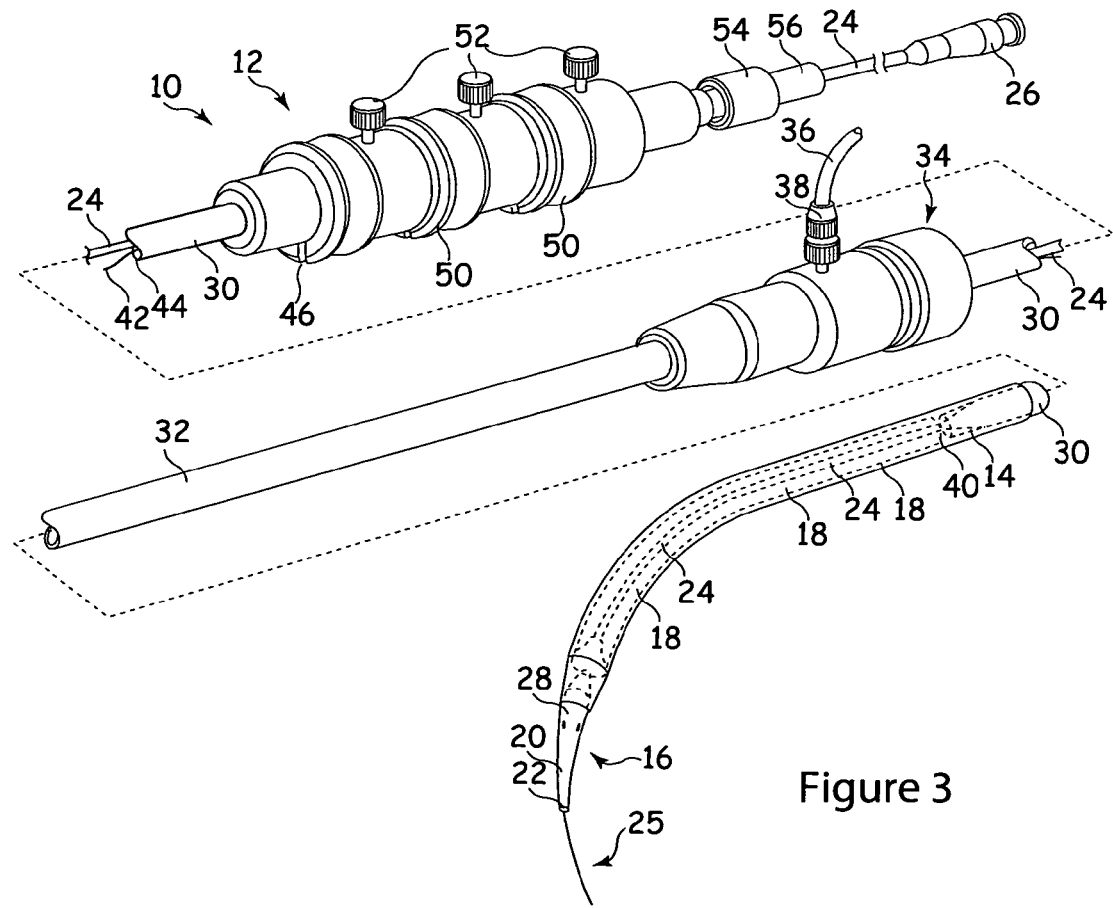

Referring now to FIGS. 2 and 3, there is shown an example of introducer of the type used in the deployment of stent-grafts of the form shown in FIG. 1. The introducer 10 includes an external manipulation section 12, a distal attachment region 14 and a proximal attachment region 16. The distal attachment region 14 and the proximal attachment region 16 secure the distal and proximal ends of the implant 18, respectively. During the medical procedure to deploy the implant 18, the distal and proximal attachment regions 14 and 16 will travel through the patient's lumen to a desired deployment site. The external manipulation section 12, which is acted upon by a surgeon to manipulate the introducer, remains outside of the patient throughout the procedure.

The proximal attachment region 16 of the introducer 10 includes a dilator tip 20, which is typically provided with a bore 22 therein for receiving a guide wire 25 of conventional type. The longitudinal bore 22 also provides a channel for the introduction of medical reagents. For example, it may be desirable to supply a contrast agent to allow angiography to be performed during placement and deployment phases of the medical procedure.

A guide wire catheter 24, conventionally made from a flexible thin walled metal tube, is fastened to the dilator tip 20. The guide wire catheter 24 is flexible so that the introducer 10 can be advanced along a relatively tortuous vessel, such as a femoral artery, and so that the distal attachment region 14 can be longitudinally and rotationally manipulated. The guide wire catheter 24 extends through the introducer 10 to the manipulation section 12, terminating at a connection device 26, in conventional manner.

The connection device 26 is designed to accept a syringe to facilitate the introduction of reagents into the inner catheter 24. The guide wire catheter 24 is in fluid communication with apertures 28 in the flexible dilator tip 20. Therefore, reagents introduced into connection device 26 will flow to and emanate from the apertures 28.

A pusher sheath or rod 30 (hereinafter referred to as a pusher member), typically made from a plastics material, is mounted coaxial with and radially outside of the guide wire catheter 24. The pusher member 30 is "thick walled", that is the thickness of its wall is preferably several times greater than that of the guide wire catheter 24.

A sheath 32 extends coaxially over and radially outside of the pusher member 30. The pusher member 30 and the sheath 32 extend distally to the manipulation region 12.

The implant 18, which may be a stent, a stent-graft or any other implant or prosthesis deliverable by this device 10, is retained in a compressed condition by the sheath 32. The sheath 32 extends distally to a sheath manipulator and haemostatic sealing unit 34 of the external manipulation section 12. The haemostatic sealing unit 34 includes a haemostatic seal (not shown) and a side tube 36 held to the unit 34 by a conventional luer lock 38.

The sheath manipulator and haemostatic sealing unit 34 also includes a clamping collar (not shown) that clamps the sheath 32 to the haemostatic seal and a silicone seal ring (not shown) that forms a haemostatic seal around the pusher rod 30. The side tube 38 facilitates the introduction of medical fluids between the pusher rod 30 and the sheath 32. Saline solution is typically used.

During assembly of the introducer 10, the sheath 32 is advanced over the proximal end of the dilator tip 20 of the proximal attachment region 16 while the implant 18 is held in a compressed state by an external force. A suitable distal attachment (retention) section (not visible in this view) is coupled to the pusher rod 30 and retains a distal end 40 of the prosthesis 18 during the procedure. The distal end of the prosthesis 18 is provided with a loop (not shown) through which a distal trigger wire 42 extends. The distal wire also extends through an aperture (not shown in FIGS. 1 and 2) in the distal attachment section 40 into an annular region 44 between the inner catheter 24 and the pusher rod 30. The distal trigger wire 42 extends through the annular space 44 to the manipulation region 12 and exits the annular space 44 at a distal wire release mechanism 46.

A proximal portion of the external manipulation section 12 includes at least one release wire actuation section 50 mounted on a body 48, in turn mounted onto the pusher member 30. The guide wire catheter 24 passes through the body 48. The distal wire release mechanism 46 and the proximal wire release mechanism 50 are mounted for slidable movement on the body 48.

The positioning of the proximal and distal wire release mechanisms 46 and 50 is such that the proximal wire release mechanism 46 must be moved before the distal wire release mechanism or mechanisms 50 can be moved. Therefore, the distal end of the implant 18 cannot be released until a self-expanding zigzag stent thereof has been released. Clamping screws 52 prevent inadvertent early release of the prosthesis 18. A haemostatic seal (not shown) is included so that the release wires can extend out through the body 48 without unnecessary blood loss during the medical procedure.

A proximal portion of the external manipulation section 12 includes a pin vise 54 mounted onto the proximal end of the body 48. The pin vise 54 has a screw cap 56. When screwed in, vise jaws (not shown) of the pin vise 54 clamp against or engage the guide wire catheter 24. When the vise jaws are engaged, the guide wire catheter 24 can only move with the body 48 and hence it can only move with the pusher member 30. With the screw cap 56 tightened, the entire assembly can be moved together as one piece.

Once the introducer assembly 12 is in the desired deployment position, the sheath 32 is withdrawn to just proximal of the distal attachment section 14. This action releases the middle portion of the implant 18, in this example a stent or stent-graft, so that it can expand radially. Consequently, the stent or stent-graft 18 can still be rotated or lengthened or shortened for accurate positioning. The proximal end self-expanding stent however, is still retained at the dilator tip 16 by means of the release wires. Also, the distal end of the stent or stent-graft 18 will still retained within the sheath 32.

Next, the pin vise 54 is released to allow small movements of the guide wire catheter 24 with respect to the pusher rod 30 to allow the stent or stent-graft 18 to be lengthened, shortened, rotated or compressed for accurate placement in the desired location within the lumen. X-ray opaque markers (not shown) may be placed along the stent or stent-graft 18 to assist with placement of the prosthesis.

When the proximal end of the stent or stent-graft 18 is in place, the proximal trigger wire is withdrawn by distal movement of the proximal wire release mechanism. The proximal wire release mechanism 50 and the proximal trigger wire can be completely removed by passing the proximal wire release mechanism 50 over the pin vise 54, the screw cap 56 and the connection unit 26.

Next, the screw cap 56 of the pin vise 54 is loosened, after which the inner catheter 24 can be pushed in a proximal direction to move the dilator tip 20 in a proximal direction. When the dilator tip 20 no longer surrounds the end of the stent or stent-graft 18, it expands to engage the lumen walls of the patient. From this stage on, the proximal end of the stent or stent-graft 18 cannot be moved again.

Once the proximal end of the stent or stent-graft 18 is anchored, the sheath 32 is withdrawn distally of the distal attachment section 14, which withdrawal allows the distal end of the stent or stent-graft 18 to expand. At this point, the distal end of the stent or stent-graft 18 may still be repositioned as needed.

As will be apparent in particular from FIG. 3, the distal end of the introducer is flexible, so as to be able to follow a tortuous path of a patient's vasculature, as well as in some applications to locate a stent-graft in a curved portion of a lumen such as the aortic arch. The distal end curves, however, by being pulled into this configuration as a result of curving of the guide wire, which is itself urged into a curved shape by the curvature of the lumen. As a result of this, the distal end of the introducer tends to follow the outside of any curve. When deployment occurs in such a situation, as it does in the aortic arch for example, the stent-graft can become improperly located, as in the example of FIG. 1.

Figure 4:
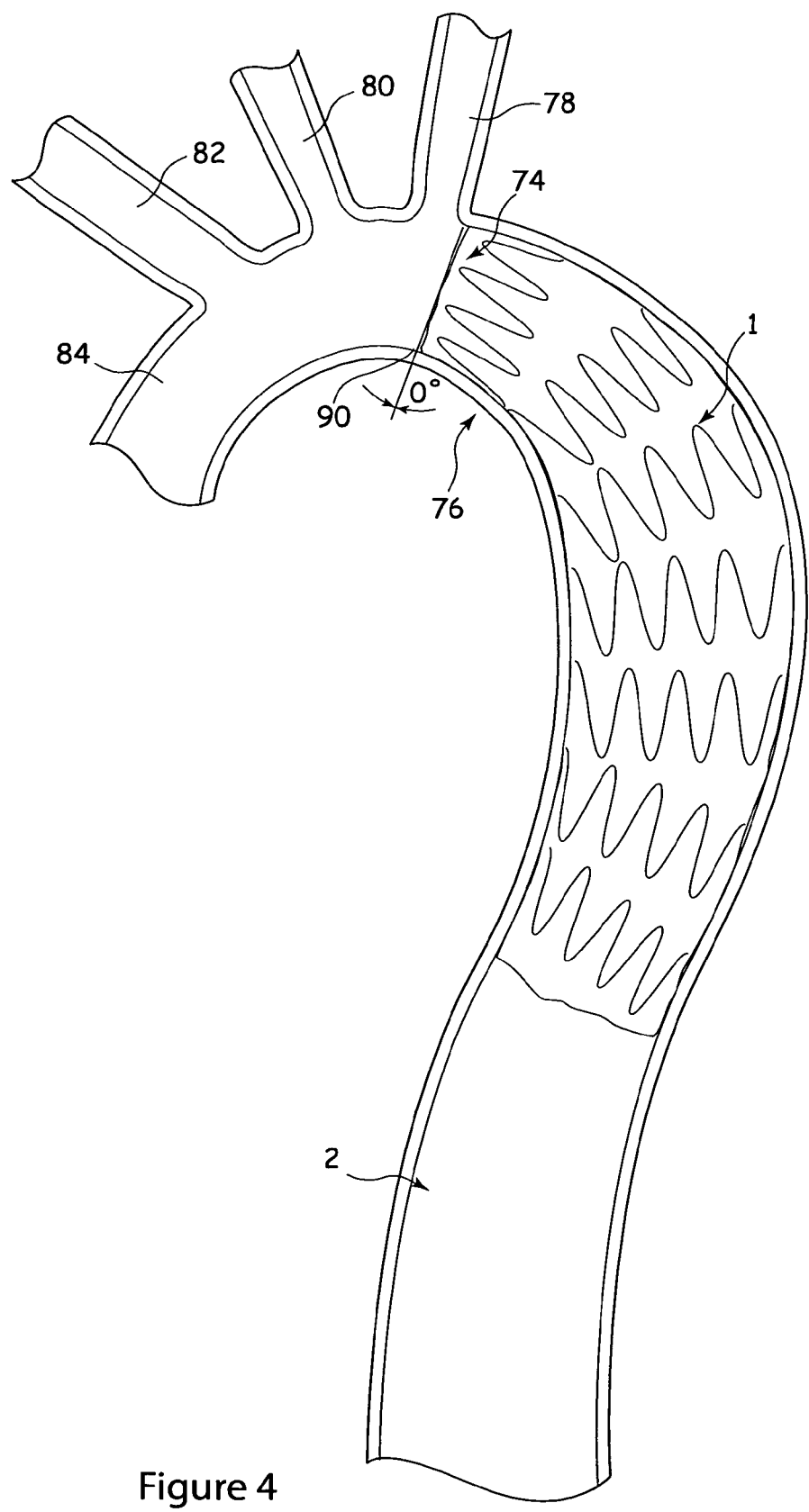
FIG. 4 is a view similar to that of FIG. 1 showing the ideal placement of a stent-graft within the aortic arch.

The optimal configuration for the stent-graft is shown in FIG. 4. As can be seen, the stent-graft 1 is properly deployed in an aorta 2 of a patient. The proximal end 74 of the stent-graft 1 is positioned in the aortic arch 76, just short of the left subclavian artery 78, in this example, although in some circumstances may extend to beyond the left subclavian artery 78, as well as beyond the left common carotid artery 80 and the brachiocephalic artery 82 and into the ascending aorta 84. Fenestrated or branched stent-grafts for such applications are known in the art.

It will be noted that the proximal end 74 lies correctly in FIG. 4, so as to be perpendicular to the vessel. In this orientation, it is properly sealed to the vessel wall all around its circumference, including at the radially internal side 90, leaving no gap for blood leakage.

Precise and reliable placement of the proximal end 74 of the stent-graft 1 would allow this to be fitted in a much shorter neck length of vessel wall compared to the less reliable prior art systems.

The applicant's earlier U.S. Pat. No. 6,974,471 describes a variety of mechanisms for imparting a curvature to the stent-graft at the moment of its deployment, primarily by mechanisms which act to pull on the proximal (upstream) end of the stent-graft.

The present invention seeks to address the problems encountered with prior art introducer systems and in a way which can enhance the fitting of the stent-graft into a lumen, particularly at the aortic arch and other highly curved regions of vasculature.

Figure 5:
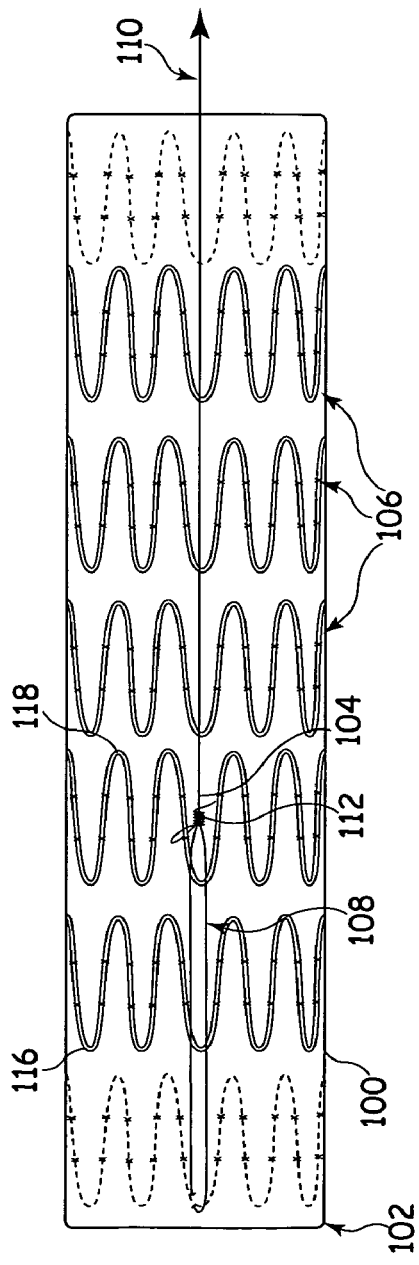
FIG. 5 is a schematic diagram showing the general arrangement of a suture loop used in the preferred embodiments of the invention.

Referring to FIG. 5, there is shown in schematic form a mechanism for curving the proximal end 102 of a stent-graft 100. The mechanism 104 includes a loop 108 of suture thread located on one side of the stent-graft 100 and which is wrapped around a plurality of stent rings 106 of the stent-graft 100 in various arrangements described below. The suture loop 108 includes a free end 110 which can be pulled so as to tighten the loop 104 and thus to pull the proximal end 102 of the stent-graft in a distal direction, thereby to cause the stent-graft 100 to curve in the manner shown in FIG. 6.

The operation of curving the proximal end 104 of the stent-graft 100 is intended to conform the shape of the stent-graft 100 to the shape of the lumen within which it is placed. For example, for deployment in the aortic arch, as shown in FIG. 4, the stent-graft 100 is curved, by pulling on the suture loop 104, to an extent comparable to the curvature of the aortic arch. So doing better orients the proximal end 104 to the vessel wall, so as to achieve a placement of this end as close as possible to parallel with the vessel wall, such that the opening of the stent-graft at its proximal end 104 is substantially perpendicular to the vessel wall. This optimizes the seal of the proximal end 104 of the stent-graft 100 to the vessel wall and also allows the fitting of a stent-graft in vessels having only a short neck of healthy vessel wall tissue.

The suture loop 104 is provided with a knot 112 at one end through which the free end 110 passes. The knot 112 allows the thread to slide therethrough such that the loop 104 can be tightened. The knot 112 could be a slip knot, which allows the thread 110 to slide therethrough both when the end 110 is pulled in a distal direction to curve the stent-graft and also in a proximal direction when the end 110 is released. This allows the stent-graft to change its reduced its angle of curvature after deployment, for example to follow changing curvature of the lumen within which it is fitted. Slip knots suitable for this application are well known in the art. The advantage of a slip knot is that once the thread end 110 is released by the operator (typically the physician) the stent-graft can move more freely with the lumen, does not impose upon the lumen the curvature imparted to it by the suture loop 104 and is less prone to fatigue failure.

In another embodiment, the knot 112 is a self-tightening knot, such as a half-blood knot. Self-tightening knots of this type are known in the art.

A characteristic of self-tightening knots is that they allow, in this example, the end 110 to be pulled through the knot so as to reduce the length of the loop 104 and thus to pull the distal end 104 of the stent-graft 100 into a curved configuration. The knot 112 then locks the loop in place, to prevent the end 110 from sliding in the opposite, loop loosening, direction. Such a knot fixes the stent-graft in the selected angle of curvature and does not allow this to increase. It can be advantageous in cases where it is not desired to impose on the vessel a straightening force which might be imparted by the stent-graft as a result of its tendency to straighten. It can also be used to impart a particular curvature to a vessel where this is considered valuable for a particular medical condition.

Figure 6A:
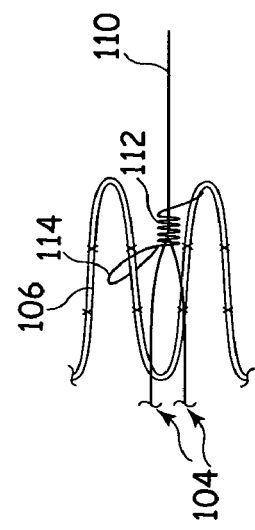
FIG. 6A shows a preferred embodiment of tying mechanism for a curvature suture loop for the stent-graft of FIGS. 5 and 6.
Figure 6:
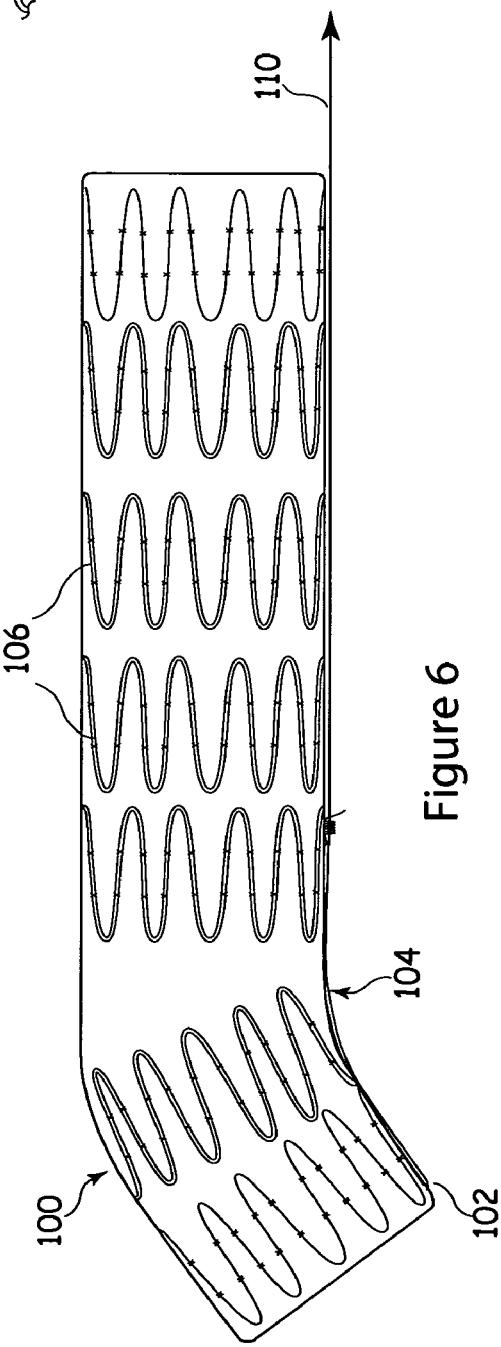
FIG. 6 is a diagram similar to FIG. 5 showing the stent-graft curved by tightening of the suture loop.

In the embodiment shown in FIG. 6A, the knot 112 is itself tied to a stent 106 of the stent graft 100, in this example by a loop of thread 114 which is sutured both to the knot 112 and to a stent strut 106 (in other embodiments the loop 114 may be sutured to the graft material of the stent-graft 100). Tying the knot 112 in this manner assists in the tightening of the loop 104. More particularly, in cases where the knot 112 is not tied in any way to the stent-graft, pulling on the end 110 will generally pull the entirety of the distal end of the loop 104, knot 112 included, in a distal direction, thus failing to tighten the loop 104 itself. For this reason it has previously been necessary to provide an element to the introducer which restrains the knot 112, typically a narrow cannula through which the end 110 passes and which has a lumen smaller than the diameter of the knot 112 such that this cannot pass into the cannula. With this solution, as the end 110 is pulled, the knot comes into abutment with the cannula and cannot move any further. Continued pulling on the end 110 tightens the loop 104. Even thought this solution allows the loop to be tightened, it is not ideal as it relies upon a cannula of no fixed position to tighten the loop.

FIG. 6A shows in better detail an embodiment of loop arrangement which can more reliably be tightened. The loop 104, knot 112 and end 110 are substantially identical to the example shown in FIGS. 5 and 6, the knot likewise being a slip knot or a self-tightening knot. The loop 114 of thread material is sutured through the knot 112 and through a stent 106 of the stent graft 100. This had the effect of tying the knot 112 to the stent-graft 100, in practice to a relatively fixed position, such that when the end 110 of the loop 104 is pulled the knot 112 cannot slide therewith and the loop 104 tightens. In effect, this solution makes it unnecessary to use a cannula as with prior art systems. Notwithstanding this, it is preferred to use a cannula as this can ensure that there is no movement of the stent-graft 100 while this is compressed to its curved configuration.

Although FIG. 6A shows the suture loop 114 threaded through a stent 106, it could equally be threaded through graft-material or through both a stent and adjacent graft material. The latter may be particularly suitable in cases in which the stent is located on the other side of the graft material relative to the thread 104-110.

Referring again to FIG. 6, it is preferred to control precisely how the stent-graft 100 is compressed to its curved configuration. This is particularly important given the fact that stent-grafts are typically formed of a plurality of stent rings 106 disposed in spaced relationship along a tube of graft material. The stent rings 106 are substantially rigid in the longitudinal direction of the stent-graft 100 and thus do not lend themselves to even curvature of the stent-graft.

FIGS. 7 to 10 show a plurality of different suture loop arrangements for controlling how the stent-graft is curved. In these Figures, the loop 104 of suture material is shown to pass around the struts of the stent rings 106 in various different ways. The loop makes use of the graft material of the stent-graft 100, although could equally rely upon sutures of the device or the stents themselves to provide anchoring points which ensure the proper positioning of the thread of the loop 104.

Where a drawing shows the thread of the loop passing at an upper position of a stent ring, this is representative of the thread being placed adjacent a peak 116 (see FIG. 5) between two struts of the stent 106, that is a proximal position; whereas when the thread is shown passing at a lower position this is representative of the thread being placed adjacent a valley 118 between two struts of the stent 106, that is in a distal position.

In FIGS. 7A to 10A the upper end of each drawing represents the proximal end 102 of the stent graft 100. For the sake of simplicity, the graft portion of the stent-graft 100 is not shown in FIGS. 7A to 10C. It will be appreciated that when the stent-graft 100 is compressed to one of the curved configurations shown in the drawings and described below, the graft material between the stents 106 will fold. Furthermore, the knot 112 is not shown in any of the drawings, for the sake of simplicity. This will, however, be provided just distal of the ends shown in the Figures and preferably, but not necessarily, tied to a stent 106 in the manner shown in FIG. 6A.

Referring first to FIG. 7A, there is shown an arrangement which ensures that the stents 106 overlie one another on the inside of the curve from the proximal end to the distal end of the stent-graft 100. In this arrangement, the loop 104 passes around a valley 108 of a strut pair of the end stent 106 of the stent graft, through the inside of the stent-graft 100, back out through a valley 118 in the next stent 106 in line and immediately back into the interior of the stent-graft 100, whereupon is passes out again through a valley 118 in the third stent 106, finally to the knot 112 (not shown in FIG. 7A).

Figure 7C:
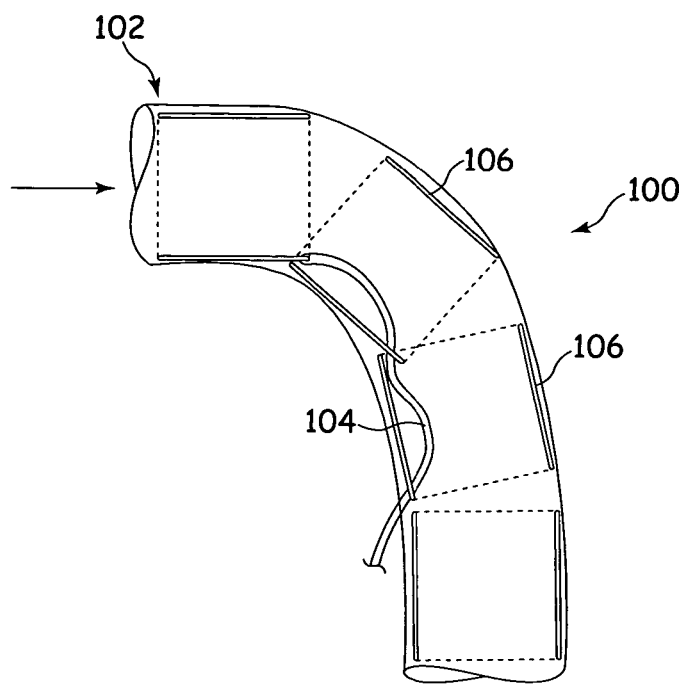

The arrangement of FIG. 7A provides for each successive stent 106 of the set of three to impart a substantially identical angle of curvature to the stent graft and for the sides of the stents 106 on the interior of the curve to slide over one another such that the trailing edge of one stent 106 overlies the leading edge of the next stent 106 in line over the curve. The effect can be seen in schematic form in FIG. 7B and in more detail in FIG. 7C.

Ensuring that the stents 106 overlie one another along the interior surface of the curve, as can be seen in FIG. 7C, minimizes flow turbulence within the stet-graft.

Figure 8C:
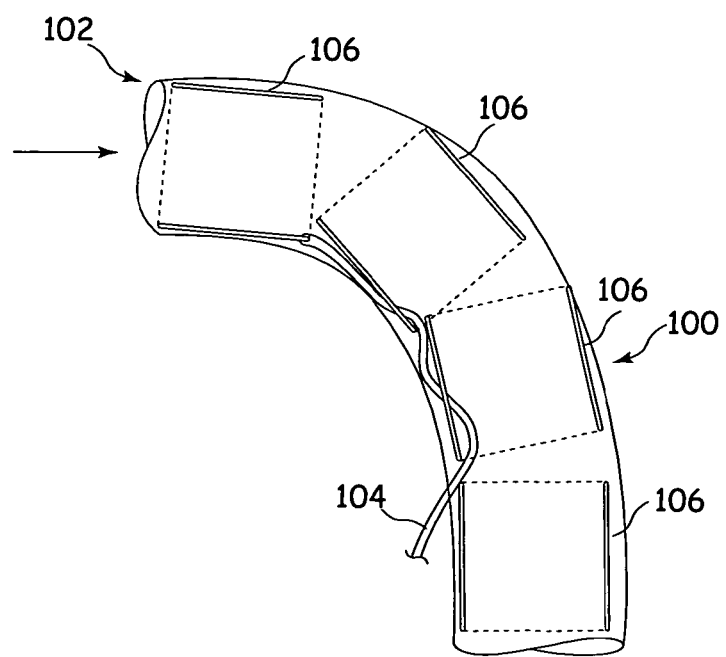

FIG. 8A shows another embodiment of loop arrangement. In this embodiment, the loop 104 passes through the valleys 118 of the three stents 106 closest to the proximal end 104 of the stent graft 100, as in the embodiment of FIG. 7B, but in this case pass such that the loop 104 overlies the stents 106 on the outside of the stent-graft 100. As can be seen in FIGS. 8B and 8C, this arrangement causes the distal end of each stent 106 to lie on the outside of the proximal end of the adjacent stent 106 in the distal direction. This arrangement, as will be seen in particular in FIG. 8C, will increase turbulence within the stent-graft when fluid flows in the direction of the arrow, that is from the proximal to the distal end of the stent-graft 100.

FIG. 9A shows an arrangement in which the loop 104 passes first through the valley of two stent struts of the end-most stent 106, through the inside of the stent-graft 100, missing completely the second strut 106, and passing next out through the peak 116 in the third stent 106 in line. The loop 104 then passes on the outside of the stent graft 100, back therein just above the a peak 116 of the fourth stent 106 and then out again just under that peak 116.

Figure 9C:
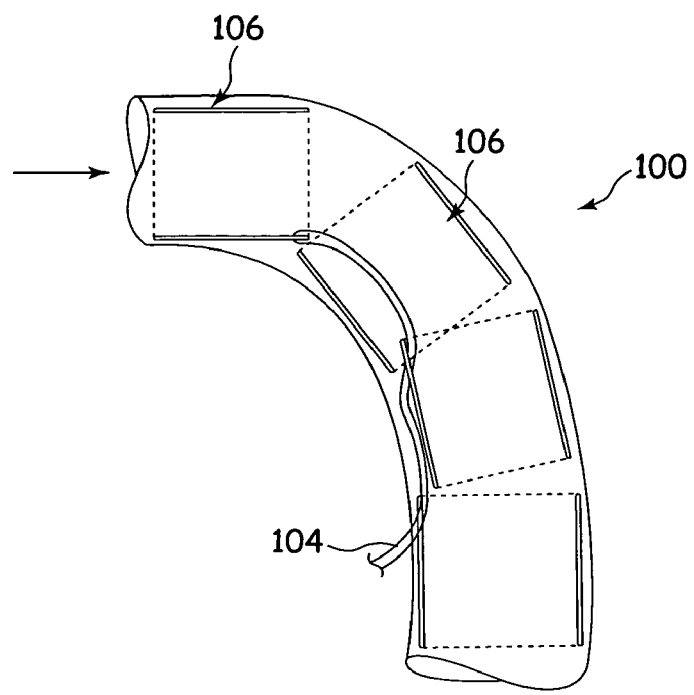

This arrangement of FIG. 9A will cause the stent-graft 100 to bend in the manner shown in FIGS. 9B and 9C, that is in a manner by which the second stent 106 will, at the inside of the curve, be forced outwardly of the first and third stents 106. This arrangement reduces the limiting effect of the section of graft-material located between the stents 106 on the degree of curvature possible in the stent-graft, in other words allows a greater curvature of the stent-graft 100. Furthermore, as the distal end of the first stent 106 from the proximal end 104 overlies the second stent 106, as can be seen in particular in the schematic diagram of FIG. 9B, there is provided a substantially uniform inner surface to the stent-graft 100 which reduces turbulence in the stent-graft 100.

FIG. 10A shows yet another embodiment of loop arrangement. In this embodiment, the loop 104 starts looped around a valley 118 in the first stent 106 at the proximal end 104 of the stent-graft 100, passes on the outside of the stent-graft 100 over the second stent 106, back into the stent-graft 100 just above a peak 116 of the third stent 106, through this peak back out of the stent graft and though a peak 116 in the fourth stent 106 in similar manner.

Figure 10C:
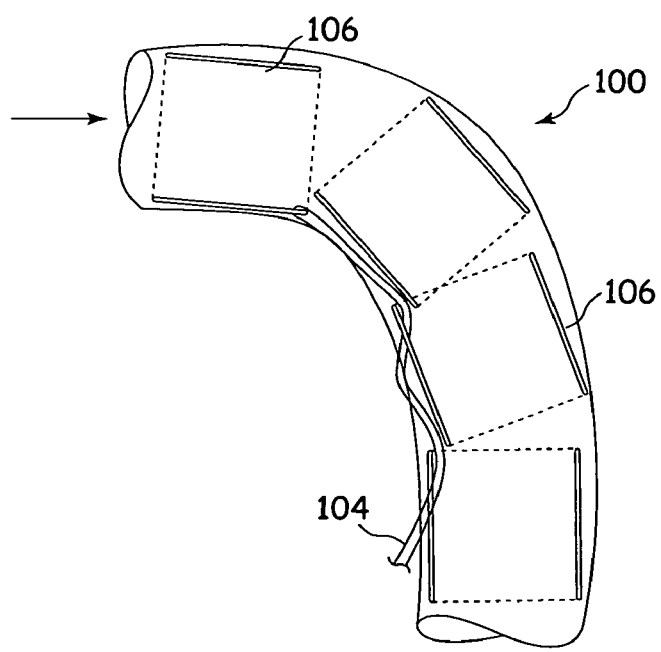

This arrangement of FIG. 10A thus omits the second stent from coupling to the loop 104 and does so in a way in which the loop 104 overlies, on the outside, this stent. The effect of this arrangement is to push the second stent 106 inwardly at the inner curve of the bend as the loop 104 is tightened, in a manner shown in schematic form in FIG. 10B and more completely in FIG. 10C. Whilst this arrangement causes the stent struts of the second stent to lie inside the stent-graft 100 in the curve, which can increase turbulence, this arrangement provides a tighter curvature with this structure of stent-graft. In particular, the second stent 106 is able to compress radially inwardly as a result of the force imparted on it by the trailing edge of the first stent 106 and the leading edge of the third strut, this compression increasing the angle by which the stent-graft can curve. In other arrangements, such as those shown in FIGS. 7A and 8A in particular, the stents are arranged evenly over an adjacent stent at one end and under an adjacent stent at the other stent, such that the stents are evenly supported and biased in compression. The relative stiffness of the stent struts limits the amount by which the stents 106 can compress in the arrangements of FIGS. 7A and 8A, whereas in the arrangement of FIG. 10A there is no such support on the second stent by one of its adjacent stents, such that it is able to compress more, thereby providing for greater curvature (smaller radius) of the overall stent-graft 100.

Referring now to FIGS. 11 and 12 in particular, there is shown a preferred embodiment of deployment element for operating the loop 104 and for imparting a curvature to the stent-graft 100. The deployment element includes a thin cannula 120 having its distal end 122 located adjacent the knot 112 of the loop 104. The cannula 120, which is preferably of flexible form and made of one of the materials known and used in the art for such purposes, extends proximally towards an external manipulation end of the introducer and in particular to a location at which it can be controlled by a physician. It is envisaged, for example, that the cannula could be fixed relative to another component of a standard introducer assembly. The cannula 121 is provided with an internal lumen 121 for the passage of the free end 110 of the loop 104 for the purposes of being able to pull this so as to tighten the loop 104 and thus to curve the stent-graft 100.

Proximate its distal end 122, the cannula 120 is provided with a slot 124 opening into the lumen 121. Located to extend through this slot 124 there is provided a tied loop 126 of suture material, which is fed around a stent strut of a stent 106 as well as around a control wire or rod 128. The tied loop 126 fixes the cannula 120 relative to the stent-graft 100 until the loop 126 is released, in a manner described below. While the cannula 120 is tied to the stent-graft 100, it is possible to impart positional control to the stent-graft 100, for example by holding the cannula 120 in position while pulling on the loop end 110. This feature is particularly advantageous in this application since the act of pulling the loop 104 will naturally tend to pull the stent-graft 100 in a downstream direction, away from the treatment site. The cannula allows the physician to use the cannula 120 to apply a pushing force against the pulling force of the loop 104 so as to keep the stent-graft 200 in position, as well as to provide for a degree of adjustment to the position of the stent-graft 100 by movement of the cannula 120.

Referring now in particular to FIGS. 12 and 13, there is shown an embodiment of mechanism for holding the loop 104, and in particular its free end 110, as well as the tied loop 126 used to tie the cannula 120 to the stent-graft 100. In this embodiment, the free end 110 is tied in a loop 130. A pulling cord 140 is provided with a looped end 142, which is fed through the looped end 130 of the thread 110. The control wire or rod 128 is fed through the loop 142 of the pull cord 140. Similarly, the tied loop 126 is also located on the control wire or rod 128. These loops, as can be seen in FIG. 12, reside within the lumen 121 of the cannula 120.

The loop 104 can be tightened by pulling on the pull chord 140, in which event the loop 142 slides down the control rod 128, pulling with it the looped end 130 and thus tightening the loop 104.

Once the stent-graft 100 has been curved to the desired extent, the cannula 120 and be removed, as well as the pull cord 140. This is achieved by retracting the control rod 128 (pulling it downwards in the views of FIGS. 12 and 13) in which event the tied loop 126 first becomes released from the rod 128, thus becoming free of the cannula 120, and in turn releases the cannula 120 from the stent-graft 100. Next, as the control rod 128 is retracted further, this releases the loop 142. The pull cord 140 can now be withdrawn, upon which the loop 130 is free to pass through the loop 130, thereby releasing the pull cord 140 from the free end 100 of the loop 104. Once this has been achieved, the cannula 120, control rod 128 and pull cord 140 can be completely removed, leaving the stent-graft 100 in place. It will be appreciated that the tied loop 126 and the tightening loop 104 will remain in place on the stent-graft 100 after the deployment procedure.

Figure 14A:
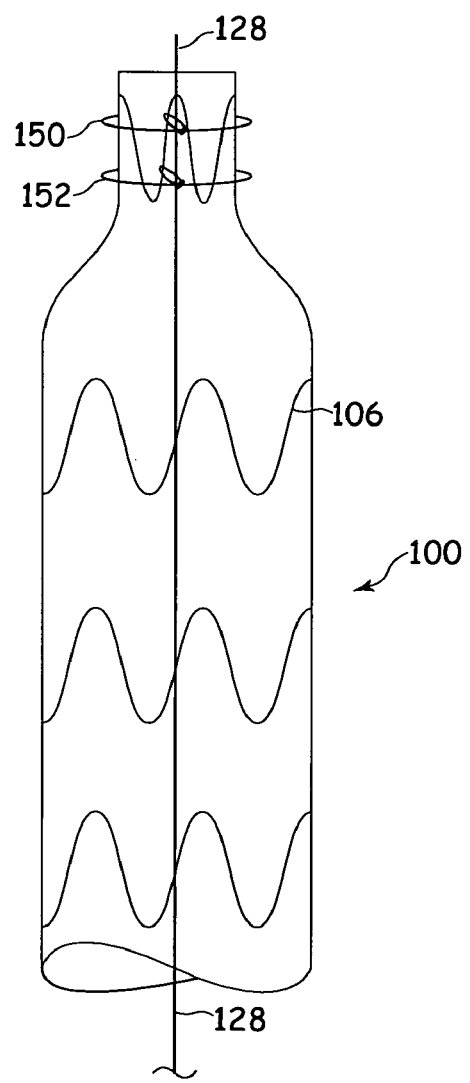
FIGS. 14A and 14B show in schematic form an embodiment of device for use in constricting the proximal end of a stent-graft during deployment.
Figure 14B:
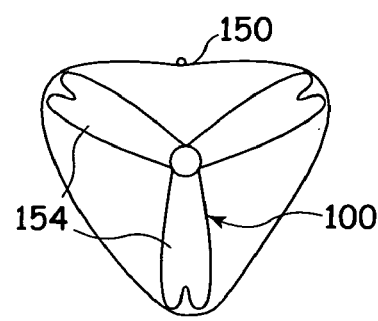

Referring now to FIGS. 14A and 14B, there is shown an embodiment of arrangement for retaining the proximal end 102 of the stent-graft 100 during its deployment. Typically, there is provided at the proximal end of the stent-graft a series of barbs which dig into the walls of the vessel so as to secure the stent-graft in place. For conventional deployment procedures the barbs tend not to present any particular difficulty as they pierce the vessel wall only when the stent-graft is in position and expanded. However, a difficulty arises in systems which provide for curving of the stent-graft and in particular by compression of the side of the stent-graft located on the inner radius of curvature during its deployment. Such systems can result in the proximal end of the stent-graft being pulled backwards as it is being curved, with the result that the barbs can scrape along the vessel, damaging the vessel wall.

In FIGS. 14A and 14B, there is shown a system for constraining the proximal end 102 of the stent-graft 100 after this has been released from the outer sheath and the inner catheter upon which is it carried to the deployment site. The system provides, in this embodiment, two threads 150, 152 of suture material which are disposed radially around the most proximal stent 106. The threads 150, 152 are of a length which is less than the uncompressed diameter of the stent-graft 100, as shown, such that they retain this in a compressed or wrapped state until they are released.

As can be seen, the threads are provided with looped ends which are located on a control wire or rod 128, which may be the same as the control rod 128 shown in FIGS. 11 to 13.

Referring in particular to FIG. 14B, the stent-graft 100 is typically wrapped for delivery, in conventional manner, by pulling the stent-graft inwards at three or more radial positions, such that it adopts a propeller or wing shaped profile when viewed along its axis, as can be seen in FIG. 14B. The threads 150, 152 will thus press in the ends of the "wings" 154 of the stent-graft 100. With this arrangement, thus, a proportion of the barbs provided on the outside of the stent-graft 100 will be held within the envelope of the wings 154. Only a few barbs may extend to the tips of the wings 154, which the threads 150, 152 can keep held in the constricted configuration. In some embodiments the stent-graft 100 could be manufactured so as to have no barbs at the tips of the wings when held wrapped as shown in FIG. 14B, in which case there will be no risk of barbs snagging the vessel wall as the stent-graft 100 is curved.

With this arrangement, the proximal end 112 of the stent-graft 100 can be kept constrained throughout the procedure of curving the stent-graft, such that there is no risk of the barbs damaging the vessel wall. That is, threads 150, 152 can be kept in their constraining arrangement while the stent-graft 100 is being curved. Once the stent-graft 100 has been curved to the desired extent, the threads 150, 152 can be released, in this embodiment by withdrawing the control rod 128, upon which the looped ends can free themselves from one another and allow the proximal end of the stent-graft 100 to expand such that this contacts the vessel wall and the barbs provided can penetrate the vessel wall to fix the stent-graft 100 in place. As the stent-graft 100 has already been curved, there is minimal movement of the stent-graft 100 along the vessel wall and thus minimization of damage, if any, to the vessel wall.

What is claimed is:

1. An implantable medical device including a compressible and curvable structure; a loop of suture material, the loop including a first end closed in a knot and a second end passing through the knot and able to slide therein at least in a loop tightening direction, the loop being fitted to the device such that tightening of the loop causes the device to be curved; and including a tie element which ties the knot to a part of the medical device.

2. An implantable medical device according to claim 1, wherein the knot is one of a slip knot and a self tightening knot.

3. An implantable medical device according to claim 1, wherein the device is provided with a plurality of stents coupled to one another by resilient means, the loop being fitted so as to be held to a surface of the device at a plurality of positions adjacent portions of said stents so as to pull said stents together such that at least some of said stents overlap one another in a predetermined manner when the loop is tightened so as to cause folding of the resilient means between adjacent stents.

4. An implantable medical device according to claim 3, wherein the device is a stent-graft, the resilient means being graft fabric.

5. An implantable medical device according to claim 3, wherein the loop is fitted to the device so as to cause overlap of adjacent stents held in the loop.

6. An implantable medical device according to claim 5, wherein the loop is fitted so as to cause trailing ends of stents to slide over leading edges of their adjacent stents in a direction from a proximal end to a distal end of the device.

7. An implantable medical device according to claim 5, wherein the loop is fitted so as to cause trailing ends of stents to slide under leading edges of their adjacent stents in a direction from a proximal end to a distal end of the device.

8. An implantable medical device according to claim 3, wherein the loop is fitted so as to cause at least one of the stents to be pulled between stents located either side thereof.

9. An implantable medical device according to claim 8, wherein said at least one stent is pulled to a position underlying the stents adjacent thereto so as to lie on an outside of the device.

10. An implantable medical device according to claim 8, wherein said at least one stent is pulled to a position overlying the stents adjacent thereto so as to lie on an outside of the device.

11. An implantable medical device according to claim 1, wherein the loop is fitted to the medical device so as to pass a plurality of times between an internal space of the device to outside thereof, thereby to cause the device to compress or fold in locations between transitions points of the loop from the inside to the outside of the device.

12. An implantable medical device according to claim 1, including a constriction device for constricting a proximal end of the device during curvature thereof.

13. An implantable medical device according to claim 12, wherein the constriction device includes at least one thread wrapped around the proximal end of the device, said at least one thread being releaseable from a constricting arrangement to allow full deployment of the device.

14. An implantable medical device including a compressible and curvable structure, a loop of suture material, the loop including a first end closed in a knot and a second end passing through the knot and able to slide therein at least in a loop tightening direction, the loop being fitted to the device such that tightening of the loop causes the device to be curved, wherein the device is provided with a plurality of stents coupled to one another by resilient means, the loop being fitted so as to be held to a surface of the device at a plurality of positions adjacent portions said stents so as to pull said stents together such that at least some of said stents overlap one another in a predetermined manner when the loop is tightened so as to cause folding of the resilient means between adjacent stents.

15. An implantable medical device according to claim 14, wherein the device is provided with a plurality of stents coupled to a flexible fabric material, the loop being fitted so as to pass from the outside to the inside or vice versa of the device adjacent portions said stents so as to pull said stents to cause folding of the fabric material between adjacent stents upon tightening of the loop.

16. An implantable medical device according to claim 15, wherein the device is a stent-graft.

17. An implantable medical device according to claim 15, wherein the loop is fitted to the device so as to cause overlap of adjacent stents held in the loop.

18. An implantable medical device according to claim 17, wherein the loop is fitted so as to cause trailing ends of stents to slide over leading edges of their adjacent stents in a fluid flow direction of the device.

19. An implantable medical device according to claim 17, wherein the loop is fitted so as to cause trailing ends of stents to slide under leading edges of their adjacent stents in a fluid flow direction of the device.

20. An implantable medical device according to claim 15, wherein the loop is fitted so as to cause at least one of the stents to be pulled between stents located on either side thereof.

21. An implantable medical device according to claim 20, wherein said at least one stent is pulled to a position underlying the stents adjacent thereto so as to lie on an outside of the device.

22. An implantable medical device according to claim 20, wherein said at least one stent is pulled to a position overlying the stents adjacent thereto so as to lie on an inside of the device.

23. An implantable medical device including a compressible and curvable structure, at least one loop of suture material, the loop including a first end closed in a knot and a second end passing through the knot and able to slide therein at least in a loop tightening direction, the loop being fitted to the device such that tightening of the loop causes the device to be curved, including a tie element which ties the knot to a part of the medical device, and a loop of suture material provided around a proximal end of the medical device, the proximal-end loop having an operable length less than the diameter of the proximal end of the medical device so as in use to constrict radially the proximal end of the medical device during deployment.

24. An implantable medical device according to claim 23, wherein the loop of suture material is able to be held in a constricting configuration during curvature of the medical device.

* * * * *